United States Patent
Chovan et al.

(10) Patent No.: US 6,714,306 B1
(45) Date of Patent: *Mar. 30, 2004

(54) SENSOR FOR OPTICALLY SENSING AIR BORNE ACOUSTIC WAVES

(75) Inventors: Joseph Lawrence Chovan, North Syracuse, NY (US); Martin Francis Lowry, Liverpool, NY (US); Evelyn Hope Monsay, Brewerton, NY (US); William Arthur Penn, Baldwinsville, NY (US); William Pattee Whyland, Marcellus, NY (US); Lawrence Richard Snowman, Liverpool, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 1,826 days.

This patent is subject to a terminal disclaimer.

(21) Appl. No.: 06/864,481

(22) Filed: May 19, 1986

(51) Int. Cl.$^7$ ................................................. G01B 9/02
(52) U.S. Cl. ....................................... 356/484; 356/517
(58) Field of Search ........................ 73/655, 656, 657; 356/349, 361, 484, 517; 367/149, 140, 153

(56) References Cited

U.S. PATENT DOCUMENTS

| 3,782,176 A | 1/1974 | Jacobs |
| 3,879,988 A | 4/1975 | Jacobs |
| 4,313,185 A | * 1/1982 | Chovan .................. 356/349 X |
| 4,422,167 A | * 12/1983 | Shajenko ................ 367/153 X |

OTHER PUBLICATIONS

R. Kristal, "Bragg Cell Heterodyne Interferometry of Fast Plasma Events", Nov. 1976.*

"On the Feasibility of Detecting Low Level Acoustic Signals in the Ocean by Use of a Laser Heterodyne Detector" by Sam Hanish (NRL Memorandum Report 3319) by the Naval Research Laboratory, dated Mar. 1, 1976.

* cited by examiner

Primary Examiner—Davis L. Willis
Assistant Examiner—Matthew W. Koren
(74) Attorney, Agent, or Firm—Patrick M. Hogan

(57) ABSTRACT

The present invention relates to an optical sensor of air borne acoustic waves. The sensor comprises means for producing mutually coherent optical sampling and reference beams, which may be combined to form an intermediate frequency carrier, the sampling beam being exposed to the acoustic field, in which acoustic wave induced density variations occur. These density variations produce a variation in the index of refraction and thereupon a phase modulation of the sampling beam. This phase modulation may be recovered by an optical detector and a phase detector as an electrical signal representative of the acoustic signal.

The invention has application to security systems.

3 Claims, 2 Drawing Sheets

US 6,714,306 B1

SENSOR FOR OPTICALLY SENSING AIR BORNE ACOUSTIC WAVES

RELATED APPLICATION

The present invention is related to the application of Monsay, Penn, and Winfield, assigned to the Assignee of the present application, and entitled "Sensor And An Array of Sensors For Optically Sensing Water Borne Acoustic Waves" (35-HE-1514), Ser. No. 864,260 filed concurrently herewith on May 19, 1987.

BACKGROUND OF THE INVENTION

1. Field of the Invention

The present invention relates to a novel acoustic wave sensor for sensing acoustic waves in a fluid typically air. The invention employs optical techniques, and more particularly depends upon the phase modulation which occurs when coherent light is passed through a fluid in which acoustic waves occur. The phase modulation may be imposed on a carrier provided by optical heterodyning and then detected electrically. The electrical signal recovered in this manner is representative of the acoustic waves.

2. Description of the Prior Art

In the patent application of Gordon Jacobs, Ser. No. 507,528 filed Sep. 19, 1974 entitled "Laser Hydrophone and Virtual Array of Laser Hydrophones", an acoustic sensor employing optical techniques was earlier proposed. The sensor, which was termed a "hydrophone", since it was designed for use in water, employed a laser beam which was focused on a small "focal" volume of water in which natural light scattering matter was suspended. The scattering matter, which vibrates in synchronism with any acoustic waves present, produces a phase modulation of the scattered light. The phase modulation was then recovered by optical heterodyne and sensitive phase demodulation techniques. The Jacobs arrangement contemplated both single hydrophones and arrays of hydrophones. In general, optical arrays, such as the Jacobs arrays, produce less hydrodynamic disturbance than the known large area piezoelectric arrays.

The Jacob's arrangement was dependent upon a "doppler" type shift in frequency or phase, the doppler shift being caused by particle motion, toward and away from the sensing beam. Thus the maximum sensitivity was obtained by pointing the laser beam in a direction toward the source of acoustic waves and perpendicular to the wave fronts.

The present invention shares certain of the objectives and in using optical techniques, certain of the means of the foregoing Jacobs' invention.

The Jacobs invention is unlike the present invention which has application to the detection of acoustic waves in the air. The present invention has application to security systems, as for instance in the monitoring of sounds occurring along the perimeter of a property.

SUMMARY OF THE INVENTION

Accordingly it is an object of the present invention to provide an improved sensor of acoustic waves occurring in a fluid medium.

It is another object of the present invention to provide an improved optical acoustic sensor for sensing air borne acoustic waves.

These and other objects of the invention are achieved in an optical acoustic sensor comprising means for producing mutually coherent optical sampling and reference beams; optical means including an aperture at which the path of the sampling beam into the air is initiated and after reflection is terminated, and light reflective means arranged in the path of the sampling beam for reflecting significant sampling beam energy back via the aperture.

The optical acoustic sensor further comprises an optical detector for coherently combining the reflected sampling beam with the reference beam to form an electrical heterodyne signal, phase modulated as result of the acoustic wave induced variation in the index of refraction, and finally a phase detector coupled to the output of the optical detector for detecting the acoustic wave induced phase variation of the sampling beam and thereby recovering an electrical signal representative of the acoustic waves.

In accordance with the invention, the initial and reflected portions of the sampling beam path between aperture and the light reflective means are oriented with a substantial component parallel to the acoustic wavefronts of the acoustic waves. For maximum sensitivity, the sampling beam path is parallel in the farfield or tangential in the nearfield to the acoustic wave fronts. With a substantial component parallel to the acoustic wave front, the sampling beam is exposed to an acoustic wave induced density variation of like amplitude over a portion of the path of the sampling beam. As the acoustic waves traverse the path of the beam of light, the density variation produced by the acoustic wave, causes the index of refraction of the fluid (air) to vary, and thereupon phase modulates.the sampling beam. The amount of phase modulation is in proportion to the accumulated variation in the index of refraction over the beam path.

BRIEF DESCRIPTION OF THE DRAWINGS

The inventive and distinctive features of the invention are set forth in the claims of the present application. The invention itself however together with further objects and advantages thereof may best be understood by reference to the following description and the following drawings in which

DESCRIPTION OF THE PREFERRED EMBODIMENTS

Figure 1:
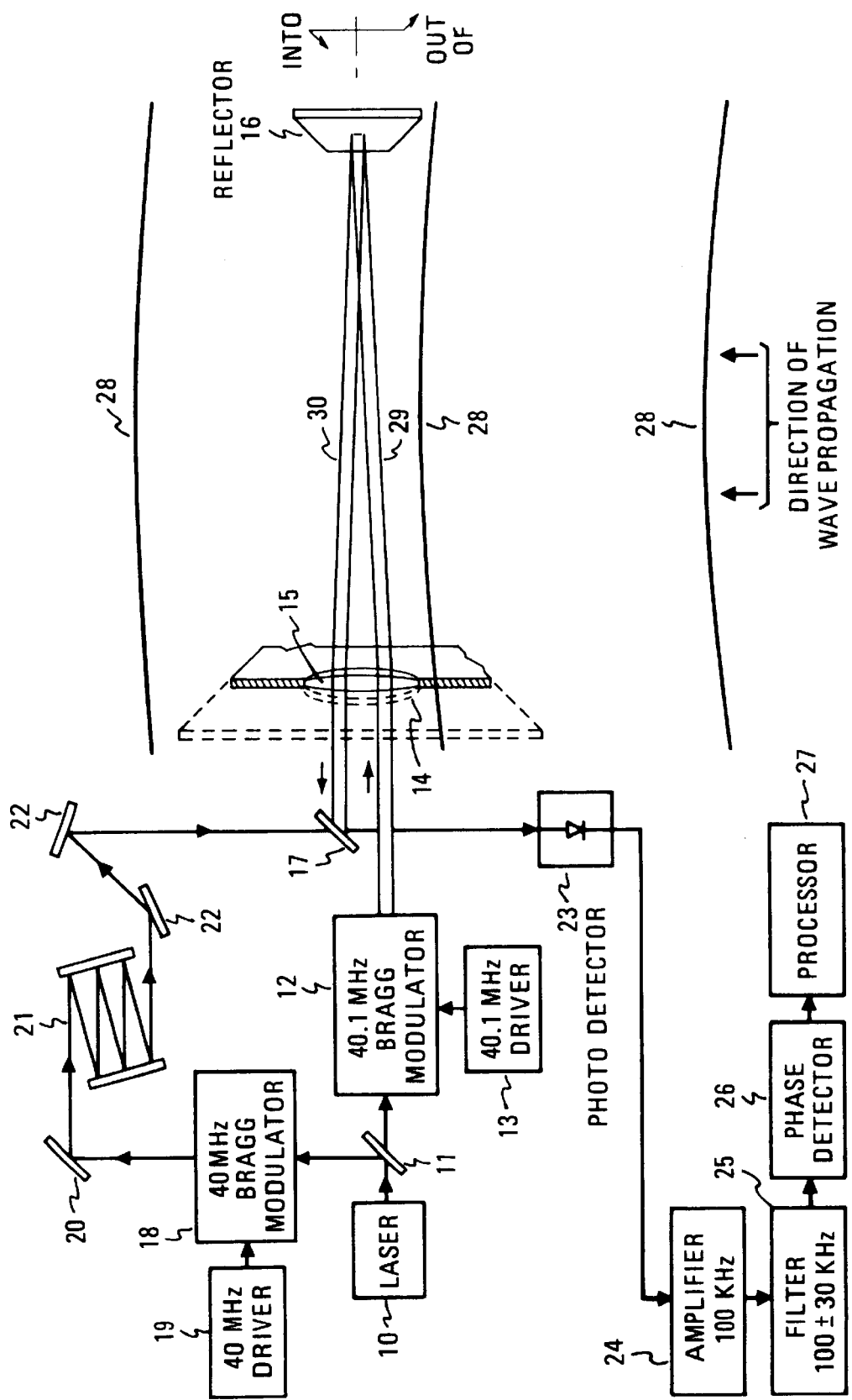
FIG. 1 is an illustration, partially in block diagram format and partially in perspective, of a single optical acoustic sensor for optically sensing air borne acoustic waves.

An optical acoustic sensor for optically sensing fluid borne acoustic waves is illustrated in FIG. 1. The sensor has as its principal optical, or light handling, components, the elements 10 to 23, and as its principal electrical or electrical signal handling components, the elements 24 to 27. The fluid, for instance air, in which the acoustic waves to be optically detected occur, is portrayed in the righthand portion of FIG. 1, with the acoustic wavefronts bearing the reference numeral 28. The source of acoustic wavefronts is not shown, being beyond the area of the illustration. (As will be explained, the features depicted in the righthand position of FIG. 1 are shown with substantial distortion in scale.)

The optical elements produce a coherent optical beam which is projected into the fluid in which the acoustic waves occur, and recover a reflected optical beam which is phase modulated by its exposure to the acoustic waves. The process entails formation of an optical heterodyne in which a sampling "beam" is projected into the fluid and recovered by reflection, while a reference beam at an offset frequency is prepared to form an optical heterodyne with the returning sampling beam. The acoustic wave induced optical phase modulation is recoverable from this heterodyne. The optical heterodyne frequency is set for convenient recovery in an electrical format of the phase modulation at the photodetector 23. The heterodyne frequency may not exceed the bandwidth of the photodetector. The electrical components, which operate upon the modulated optical signal after conversion to an electrical format, prepare the signal for display, aural reproduction, or other utilization.

The optical elements of the optical acoustic sensor, which enter into the formation and recovery of the sampling beam, include the laser 10, a first beamsplitter 11, a first (plus) 40.1 Mhz Bragg modulator 12, with an accompanying 40.1 Mhz driver 13, and optical means including an apertured barrier 14 and an optional collimating lens 15 at the interface with the air in which the acoustic waves occur. A remote reflector 16 is provided at a fixed distance from the optical means 14. The optical means 14, 15, also in the return path of the sampling beam, is followed by the beam splitter 17, and the photodetector 23, which is the last optical element of the system.

The optical elements which enter into the formation of the reference beam include the beam splitter 11, at which the reference beam is separated from the sampling beam at the output of the laser 10, a second plus (40 Mhz) Bragg modulator 18, with an accompanying 40 Mhz driver 19, a mirror 20, an optical delay 21 equal to the delay encountered in the sampling process, a pair of additional mirrors 22 for beam alignment purposes, a beam splitter 17 used for combining the reference beam with the returning sampling beam, (the actual optical heterodyne appearing at the surface of the photo-detector 23), and the photodetector 23 the last optical element of the optical system, as noted above. The optical heterodyne, appearing at the photodetector 23, is an electrical signal phase modulated by the acoustic wave.

The electrical processing elements following the photodetector 23 consist of an amplifier 24, a narrow band filter 25 (100 Khz+30 Khz), a phase detector for recovering phase and amplitude information from the acoustic wave, and a processor 27 in which further processing occurs prior to the final presentation of the information in a display or reproducer.

As previously noted, the acoustic waves of interest are illustrated in the right hand portion of FIG. 1 in which the air environment is depicted between the apertured partition and the collimator (14, 15) on the one hand, and the mirror 16 on the other hand. In the figure, the sampling beam (29, 30) proceeds to the right in a horizontal plane, (the illustration being a plan view looking toward the ground from a position above the ground) the sampling beam continues until it impinges on the reflector 16 and then returns on a slightly displaced but still horizontal path to the collimator 15. (The outgoing portion of the sampling beam bears the reference numeral 29 and the reflected beam the reference numeral 30.)

The acoustic waves in the illustration are intended to represent waves originating from a source beyond the bottom limits of the illustration. The source of the waves is assumed to be in a horizontal plane, and the distance is sufficiently small that the wavefronts 28 have curvature. The wavefronts are also assumed to be tangential to the path of the laser beam implying that the azimuthal position of the remote source is orthogonal to the sampling beam path. The acoustic frequencies may extend over a range in excess of 300 to 1; i.e., from below 50 to above 15,000 Hz. Assuming that the speed of sound in air is 330 meters per second, the spacing between wavefronts varies from two centimeters or less at the highest frequencies to 6.6 meters or more at the lower frequencies. A reasonable figure for the path length of the optical sampling beam between the aperture and the reflector is from 10 to 200 meters, but depending upon application, may be much larger.

The scale distortion in FIG. 1 requires some discussion. The relative scale as between the distance between maxima of the acoustic waves 28 and the sampling path length from 14, 15 to 16 may accordingly be undistorted at one wavelength within the 300 fold frequency range and distorted at all other wavelengths. The lens aperture dimension and the separation between outgoing and incoming sampling beams are both drawn substantially larger than to scale, for instance in relation to the sampling path length. In continuous wave (cw) of transmission, the beams 29 and 30 should be mutually displaced at the lens 15 to facilitate their separation, but not in the amount suggested by the scale. Each beam is typically 1–5 millimeters in cross-section, and the lens 15 may be 10 to 15 millimeters in diameter. The greatest separation of the two sampling beam paths would thus be in about 10 millimeters. The beam separation is so extremely small in the scale of the drawing, as to be not readily depicted. (Assuming 1 meter equals one inch for depicting acoustic wavelengths, 10 millimeters would equal $\frac{1}{100}$ of an inch.) Thus from the practical point of view of sensing an acoustic wave at the same phase position, the wavefronts of the wave being 2 meters apart, the paths 29 and 30, which are separated at most by 10 millimeters and representing a phase error in the sonic wave of only two degrees, are practically co-incident. Even though displaced, the two parts of the sampling beam may properly be represented by a single narrow line, not treated as introducing any significant error into the phase detection process.

In the optical acoustic sensor so far described with relation to FIG. 1, continuous wave (cw) laser operation is intended, and this is facilitated by displacing the outgoing from the incoming beams on the surface of the lens 15 so as to permit separation of the light in the processor. In the processor, the optical output of the Bragg modulation 12 goes through one portion of the lens 15 and the return beam enters through another portion of the lens 15 where it is intercepted by the beam splitter 17. The displacement of the beams permits the acoustic sensor to form the heterodyne continuously, without being pulsed.

One may however employ an arrangement in which the outgoing and incoming sampling waves follow an overlapping path as they enter and return through the lens 15. In the case where the beam paths overlap, the incoming waves should return to the beam splitter at a time that the outgoing wave transmission is suspended. Pulsing would achieve this end. The pulse interval should be selected to avoid simultaneous transmission and reception at the optical path length of the optical sensor.

The optimum orientation of the beam path to the acoustic wavefront for maximum sensitivity is the tangential relationship illustrated in FIG. 1. It is assumed that the object is sufficiently close that the wavefronts 28 are curved, although tangential at some point along the sampling beam. Thus the sampling beam, which travels in a linear path across the curved acoustic wavefront, will be exposed at a substantial portion of the beam path to a acoustic wave in the same condition of compression or rarifaction. The result of exposure to the condition of a maximum compression is the production of a maximum integrated index of refraction, which results in a maximum amount of phase shift of the light beam. Similarly at some time earlier or later, the sampling beam will be similarly exposed to a fluid under the same minimum compression. Exposure to this condition produces a minimum integrated index of refraction, which results in a minimum amount of phase shift of the light beam.

The optimum orientation of the beam path for maximum sensitivity to a near field source of acoustic waves is with beam path and wavefronts tangential. In principle, greater absolute sensitivity may exist in a farfield relationship in which the wavefronts are straight lines, impinging exactly parallel to the beam path. The effect of curvature of the wavefront results in a loss in sensitivity in that only a short segment of the beam path, wavelength dependent, and in the first Fresnel zone, is effective and uncancelled. This loss in absolute sensitivity is less than the increase in power density as the source approaches the beam path, and thus the detected signal level will increase as the reciprocal of the first power of the distance. In addition, the sound source need not be in the optimum azimuthal position orthogonal to the beam path at the center of the beam path. Sensitivity falls off only when the point of orthogonality between the optical beam and the acoustic beam comes close to the end of the optical beam. After this, the sensitivity falls off as the acoustic source is no longer orthogonal anywhere to the sampling beam path, and then the fall-off is gradual and wavelength dependent. As will be shown, the photon-noise-limited sensitivity is very good, so that if there is a reasonable (uncancelled) component of the acoustic wavefront in the sampling beam path, a substantial signal may usually be obtained.

As will be better appreciated as the further embodiments of the invention are discussed, the beam path may be relatively long, giving rise to the possibility that there will be a plurality of positions along the beam path at which sound sources will occur. The sources will often be in the "near field" pattern and their wavefronts will exhibit appreciable curvature as they intersect the beam path. The wavefronts will however, be tangential to the beam at one point along the beam path, creating a first Fresnel zone sensitivity.

However, as the wavelength decreases, the Fresnel zone narrows, and the sensitivity decreases. Thus the higher frequency acoustic waves, in reducing the effective length of the beam path (i.e. the first Fresnel zone) will be attenuated more than the longer wave lengths at a given proximity of the source to the beam path (disregarding the effect of bandwidth in the electronic signal processing).

The optical acoustic sensor so far described is operable as a single unit for sensing air borne acoustic waves. In summary, the sensor may be seen to include the laser 10, the beam splitter 11, and the first 40.1 Mhz Bragg modulator 12 and its associated driver 13 for producing a coherent optical sampling beam. At the same time, the same laser 10 and same beam splitter 11, a second 40 Mhz Bragg modulator 18 and associated driver and remaining optical elements 20, 21, 22 and 17 produce a monochromatic optical reference beam, mutually coherent with the sampling beam, and assist in superimposing the reference beam upon the sampling beam at the optical detector 23.

The apertured wall 14 and collimating lens 15 constitute the optical means for initiating the path of the sampling beam into the air in which the acoustic waves are present and for terminating the path by which the reflected beam returns. The collimating lens 15 also maintains the sampling beam, while the acoustic field, at a cross-sectional dimension which is small in relation to the acoustic waves of interest. In the FIG. 1 embodiment, the collimating lens is a small lens set in an aperture of a wall.

The reflector 16 is arranged in the air in the acoustic field. It is arranged in the path of the sampling beam at a fixed distance from the lens aperture combination with an orientation set to reflect the sampling beam back almost upon itself, to the lens aperture. For efficiency, the reflector 16 may be a specular mirror, and in practice, if specular, it must be a retro-reflector, which can return the reflected beam to a position which must be exact to less than the beam width for super position with the reference beam. This accuracy is required since the reference and sampling beams must be superimposed at the photo-detector. If the distances are small and the available power adequate, a non-specular reflective surface which reflects some fraction of the beam back for imaging on the photodetector surface may also be employed.

The phase modulation is recovered by the optical detector 23 at which the sampling and reference beams are coherently combined to form the phase modulated electrical heterodyne signal. Here the basic double heterodyne approach of using a plus 40.1 and a plus 40 Mhz Bragg modulator produces a 100 Khz carrier at the photodetector output. The acoustic wave induced phase modulation of the light beam appears as a modulation upon this carrier.

The double heterodyne approach may involve either a single Bragg modulator in each of the sampling and reference beam paths as shown, or two Bragg modulators in one path. One need not, however, employ the double heterodyne approach since in many types of electrical detection circuits, a larger intermediate frequency is quite usable.

The optical acoustic sensor, which includes the amplifier 24 and filter 25 following the photodetector, is completed by a phase detector 26 coupled to the output of the optical detector. The phase detector 26 produces an electrical signal which is responsive to and replicates the acoustic waves in the acoustic field. The electrical signal, while relatively low in frequency since it corresponds to the frequencies of the acoustic waves, may be seen to contain both the instantaneous amplitude of the wave and as the amplitude is being received as a function of time, the phase of the wave. Thus the optical acoustic sensor element is adaptable for use as an element of an array of like devices, should one desire greater sensitivity and greater accuracy in determining the azimuthal position of a remote source of sound.

Figure 2:
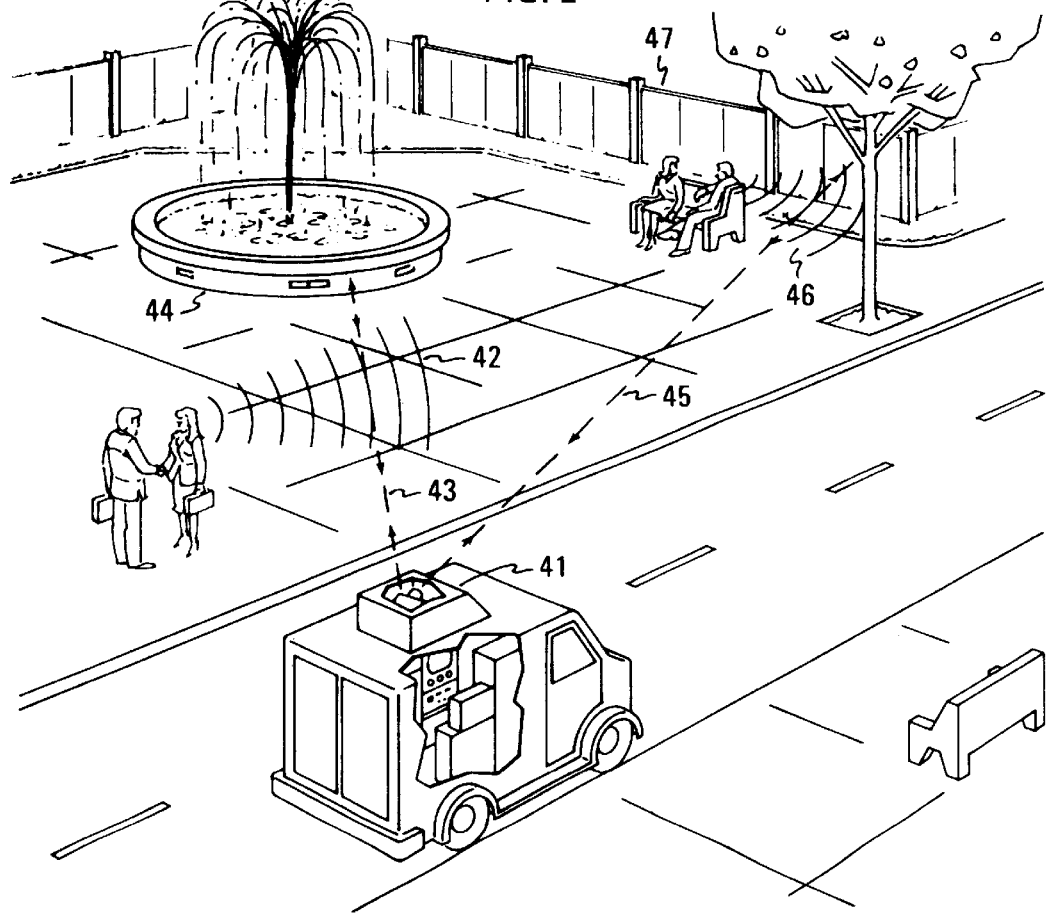
FIG. 2 is a perspective view of an optical acoustic sensor mounted upon a vehicle, for optically sensing air borne acoustic waves, as for instance conversations, the sensor using a non-specular optical reflector.

FIG. 2 is a perspective view of an optical acoustic sensor mounted upon a vehicle for optically sensing remote air borne acoustic waves, as for instance conversations, the sensor utilizing a non-specular optical reflector to return the laser beam back to the sensor.

Referring now to FIG. 2, the laser transmitter/receiver is housed in an enclosure 41 on the roof of the van seen in the foreground of the picture. Conversations are presumably taking place between the two standing individuals shown in the foreground and the acoustic waves 42 produced by the conversation are propagating across the picture to the right where they intersect the path of a laser beam shown at 43. The laser beam 43, which is initiated at the housing 41, continues through the open air to the right of the standing individuals, and is exposed there to the sonic waves 42 propagating across the path of the laser beam. The laser beam continues until it impinges on the masonry base 44 surrounding the fountain. The laser beam, upon impinging on the base 44, is in fact reflected in a number of directions, but the reflection of interest, is the backward reflection which returns a portion of the beam along essentially the same path 43, where it is intercepted at the enclosure 41 on the roof of the van.

A similar opportunity for detecting remote conversations is illustrated in relation to the seated couple in the background of the picture and to the right. A laser beam 45 is shown passing adjacent the seated individuals, where it encounters the sonic waves, depicted at 46, and then after impingement on the wall 47, some portion of the laser beam returns along essentially the same path that the beam followed originally.

Because of the non-specular nature of the reflection, the power level of the laser beam which is returned to the enclosure 41 is low. Accordingly, the transmitted laser power should be relatively high. The power level and direction of the laser beam should be selected so as to avoid injury. (The monitoring of the conversations must of course be in accordance with the laws affecting privacy.)

Figure 3:
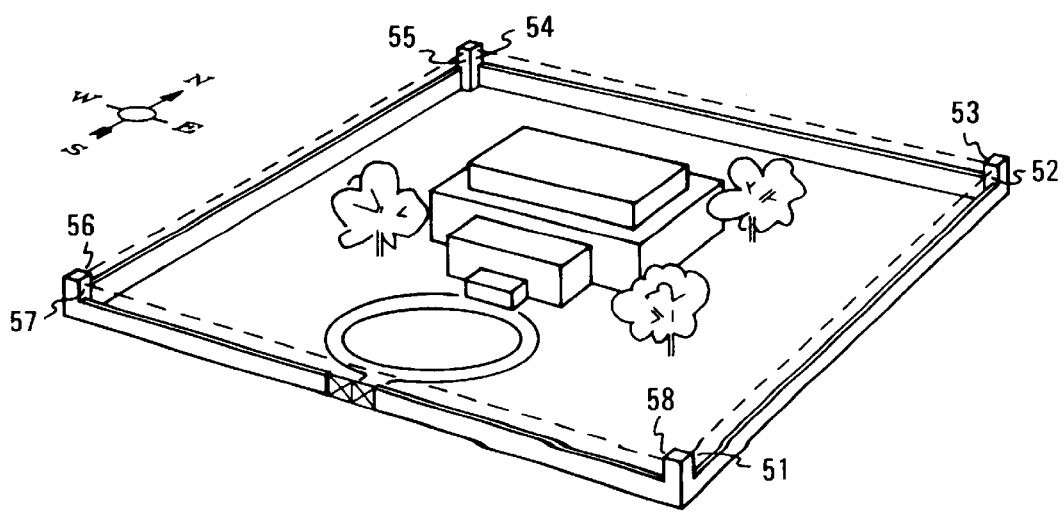
FIG. 3 is a perspective view of an arrangement employing a plurality of optical acoustic sensors mounted along consecutive line segments of a property line with optical transmitter/receivers and retro-reflectors at opposite segment ends, the arrangement being designed to optically sense air borne acoustic waves from near sources along the perimeter of a property for intrusion monitoring.

FIG. 3 is a perspective view of an arrangement for optically sensing air borne acoustic waves from near sources along the boundary of a property for intrusion monitoring. The arrangement entails a plurality of optical acoustic sensors mounted along line segments of the boundary. In the illustration, the property is four sided and therefore entails the use of four optical acoustic sensors. The sensors, as in the FIG. 1 embodiment, each consist of a optical transmitter/receiver, for example at 51 at the south-west corner of the property and a retro-reflector at 52 at the northeast corner of the property. This sensor monitors the eastern line boundary segment. Similar acoustic sensors at 53–54, 55–56, 57–58, each consisting of an optical transmitter/receiver and a retro-reflector are located at the respective ends of the northern, western and southern line segments to provide complete coverage around the perimeter of the property.

Assuming that the distances in the FIG. 3 embodiment are moderate, for example under 1,000 meters, the optical transmitters may employ low power diode lasers. The use of the specular, retro reflectors at the corners, assuming a low degree of attenuation in the beam path and good beam collimation, tends to minimize the amount of power required for reasonable acoustic sensitivity. If, however, all-weather sensitivity in mist, rain, and snow is desired, this may be accomplished by increasing the laser power, sheltering the beam path from precipitation and generally increasing the quality of collimation and reflection.

In the example, the use of low power diode lasers facilitates an eye-safe installation, the optical path traversed by the sampling beam being above the heads of prospective intruders and the optical power levels being such that casual exposure to the beam would be unlikely to produce eye injury.

The detection pattern, as has been suggested earlier, is one in which wavefronts tangential to the sampling beam path provide maximum sensitivity of response in the sensor in a first Fresnel zone. As designed, the sensor has no true blind spots. All sources along the line segments will at some point create waves tangential to the beam path producing a useful signal. At the ends of the line segments, the acoustic waves will avoid cancellation effects, and since acoustic waves propagate around corners, also be detectable.

The electrical signal processing is conveniently performed such as to reproduce the acoustic waves in a sonic format over a loudspeaker or headset to a person monitoring the system. One can, of course, employ alarm systems which are unattended except upon the activation of an alarm. Maximum sensitivity is produced as the acoustic wavelength lengthens since a longer portion of the beam path will be in the first Fresnel zone.

The beam cross-sections should be maintained to less than half an acoustic wave length to avoid attenuation of the acoustic signal due to averaging in the direction of acoustic wave propagation.

In the retro-reflector variation illustrated in FIG. 3, the maximum effective beam cross-section is set by the aperture through which both the outgoing and returning beam must pass. For "CW" laser operation, the returning beam must be offset from the reference beam at the aperture, but superimposed at the photo-detector. Accordingly, the practical beam path cross-section may be from two (the minimum) to three or four beam diameters.

The beam cross-section with a specular, retro-reflector is ordinarily dictated by the size of the available source. If low power diode lasers are to be employed, the source is a few millimeters (1–5), and the beam path cross-section for CW operation usually less than 1 centimeter. Assuming an upper acoustic frequency limit of 15 Khz, the beam cross-section may be as large as 1 cm (one-half acoustic wavelength) before a 3 db loss in sensitivity at 15 Khz would occur.

If longer paths for the sampling beam are desired, a gas laser may be employed. Here again, larger beam cross-sections may be employed with a loss in higher frequency response.

As an alternative to a CW system, one may employ a pulsed system, in which the retro-reflectors are adjusted to effect coincidence between the outgoing sampling beam at the aperture as well as at the photo-detector. In this case pulsing may be used to avoid interference at the photodetector by allowing formation of the heterodyne signal only upon the return of the sampling beam. In the pulsed system, the adjustment of essentially exact coincidence between the outgoing and returning portions of the sampling beam, makes the cross-section of the beam path essentially equal to the beam cross-section, and provides some increase in high frequency response.

With non-specular reflection, the need for significant laser power increases by several orders of magnitude. Thus, diode lasers generally will not provide sufficient optical power for such practical applications, and high power gas lasers or "slab" lasers will be required.

The calculated photon-noise-limited acoustic sensitivities of the sensors herein described are very good but hard to realize in practice. The photon-noise limited minimum detectable acoustic intensity in air, ($I_a$), (nearfield) at 1 Khz bandwidth and acoustic frequency of 1 Khz at a distance from the acoustic source of 10 meters, with a received optical power of 10 milliwatts, is calculated to be equal to $2.5 \times 10^{-18}$ watts/cm$^2$.

The photon noise limited sensitivity, which appears to represent the ultimate limit of sensitivity, exists with other often larger contributions to sensor noise. Optical bench conditions in a laboratory produce the nearest approach to photon noise limits. In a practical environment, a major contribution to sensor noise is motion of the optical transmitter/receiver, motion of the reflector and motion of the intervening air and air borne particles in the path of the beam. Equipment motion need only be of optical wavelengths in magnitude to affect sensor performance. Thus for increased sensitivity, a practical design must generally achieve a reduction in vibrations and resonances through the acoustic frequencies of interest, achieve ridgitity in the dimensions critical to sensor operation, and minimize air turbulence in the beam path of the sensor.

Theoretical predictions lead one to expect the minimum detectable acoustic intensity $I_a$ based on the quantum (photon) noise limit for the optical acoustic sensor in the farfield region to be:

$$I_a = \frac{hc_o \lambda B \rho c_a^3}{32\pi^2 P_o (n-1)^2 L^2 \mathrm{sinc}^2\left(\frac{\theta L}{\Lambda}\right)} \tag{1}$$

where h is Planck's constant
$c_o$ is the speed of light
$\lambda$ is the optical wavelength
B is the electronic bandwidth
$\rho$ is the density (of the air)
$c_a$ is the acoustic velocity in air
$P_o$ is the received optical power
$\eta$ is the quantum efficiency of the photodetector
n is the index of refraction of air
L is the interaction length of the optical beam (in the farfield region, the full length)
$\theta$ is the angle between the beam path and the acoustic wavefront, and
$\Lambda$ is the acoustic wavelength.
The "sinc" function $$\left(\text{of the form } \frac{\sin/X}{X}\right)$$

in the denominator of expression (1) expresses the directionality of the sensor under farfield conditions. The greatest sensitivity, occurs when the argument $\theta$ is equal to zero, under which condition the sinc function goes to one, its maximum value making $I_a$ smallest. The sinc function becomes zero when the argument equals unity [sinc (1)=0]. Therefore the angular increment over which the sensitivity is close to the maximum is $$\Delta\theta = \frac{\Lambda}{L}.$$

In other words, the angular increment in radians at strong sensitivity is the reciprocal of the number of acoustic wavelengths in the length of the sensor beam. Outside of this angular increment, it is expected that the sensitivity will be uselessly poor.

In the nearfield case, assuming the beam path is many acoustic wavelengths long and therefore "infinite", and assuming a tangential relationship of the acoustic wavefront to the beam path at some point along the beam path, the minimum detectable acoustic intensity in $I_a$ in air is:

$$I_a = \frac{hc_o \lambda B \rho c_a^3}{16\pi^2 P_o \eta (n-1)^2 R_o \Lambda} \tag{2}$$

Substituting values into this equation, $P_o$=10 milliwatts, $R_o$=10, acoustic frequency=1 Khz, B=1 Khz, produces the $2.5\times10^{-18}$ watt/cm$^2$ sensitivity noted earlier.

The differential acoustic pressure caused by the acoustic wave of intensity Ia may be calculated by the relation—

$$\Delta P_a = \sqrt{I_a \rho c_a} \tag{3}$$

and the acoustic intensity of $2.5\times10^{-18}$ watts/cm$^2$ corresponds to 3.25 micropascals of rms pressure.

The minimum detectable acoustic power $P_a$ emitted by the source that corresponds to this intensity can be found from the relation—

$$I_a = \frac{P_a}{4\pi R_o^2} \tag{4}$$

Substituting this in the previous equation we have—

$$P_a = \frac{\eta c_o \lambda B \rho c_a^3 R_o}{4\pi P_o \eta (n-1)^2 \Lambda} \tag{5}$$

This shows that as the distance to the source, $R_o$, decreases, the minimum power $P_a$ decreases linearly with $R_o$.

Another important situation to consider is the use of a reflector of opportunity, which in general will be of a diffuse nature. Such a surface may be modeled by "Lambertian" behavior, in which the light incident on the surface will be scattered into an entire hemisphere, with cosine angular weighting (cos $\theta$ in amplitude). As far as the backscatter (reflection along illuminating axis) which is used for detection is concerned, the behavior is equivalent to uniform scattering into $\pi$ steradians. Thus the received scattering loss factor is defined:

$$l_{scat} = \frac{P_o}{P_T} \tag{6}$$

where $P_T$ is the transmitted optical power. The scattering loss factor can be expressed:

$$l_{scat} = \frac{A_R r}{\pi R_o^2} \tag{7}$$

where $A_R$ is the optical receiver aperture area, and r is the reflectivity of the scattering surface.

Using the previous example, with r=0.1, and a receiver aperture diameter of 5 cm:

$$l_{scat} = \frac{\frac{\pi}{4}(.05)^2 \times 0.1}{\pi \times 10^2} = 6.25 \times 10^{-7} \tag{8}$$

Incorporating this loss ($P_T$=10 milliwatts) into equation (2) produces a minimum detectable acoustic intensity of $$3.95 \times 10^{-12} \text{ watts/cm}^2$$

and from equation (3) this corresponds to 4100 micro Pascals of rms pressure.

This is in the region of conversational speech levels (72 db re 1 uP).

Thus there is a dramatic loss associated with a diffuse target as compared with a retro-reflector (mirror). However the resulting sensitivity can still provide useful detection with the quantum noise assumption, and with favorable geometric relationships.

What is claimed is:

1. A sensor for optically sensing air borne acoustic waves from a remote source, comprising:
   (a) means for producing mutually coherent optical sampling and reference beams, which may be combined to form a heterodyne or homodyne intermediate frequency carrier, said sampling beam having a cross section which is small in relation to the acoustic wave lengths of interest,
   (b) optical means for defining a path for said sampling beam including an aperture through which the sampling beam enters the air in which acoustic waves are borne, and through which any light from said sampling beam passes after reflection, said aperture having a cross section which is small in relation to the acoustic wave lengths of interest,
   (c) light reflective means arranged in said path for reflecting significant sampling beam energy back via said aperture,
      said sampling beam path being oriented with a substantial component parallel to the acoustic wavefronts of interest, so that the sampling beam is exposed to an acoustic wave induced density variation of like amplitude over a substantial portion of said path, said density variation producing a variation in the index of refraction, and thereupon phase modulation of the sampling beam in proportion to the accumulated variation in the index of refraction over said beam path,
   (d) an optical detector including optical means for coherently combining said reflected sampling beam with said reference beam to form an electrical carrier, phase modulated as a result of said variation in the index of refracton and
   (e) a phase detector coupled to the output of said optical detector for detecting the acoustic wave induced phase variation of said sampling beam and thereby recovering an electrical signal representative of the acoustic waves.

2. A sensor as set forth in claim 1 wherein
said light reflective means is a specular, retro-reflector, adjusted to reflect said beam back via said aperture.

3. In combination,
   A. a plurality of sensors for optically sensing air borne acoustic waves along the boundaries of an area, each sensor comprising:
      (a) means for producing mutually coherent, optical sampling and reference beams, which may be combined to form a heterodyne or homodyne intermediate frequency carrier,
      (b) optical means for defining a path for said sampling beam including an aperture through which the sampling beam enters the air in which acoustic waves are borne, and through which any light from said sampling beam passes after reflection, said aperture having a cross section which is small in relation to the acoustic wave lengths of interest,
      (c) a specular, retro-reflector arranged in said path for reflecting the sampling beam energy back via said aperture,
         each sampling beam path being oriented such that all acoustic sources along said beam path produce acoustic wavefronts tangential to said beam path, so that the sampling beam is exposed to an acoustic wave induced density variation of like amplitude over a portion of said path, said density variation producing a variation in the index of refraction, and thereupon phase modulation of the sampling beam in proportion to the accumulated variation in the index of refraction over said beam path,
      (d) an optical detector including optical means for coherently combining said reflected sampling beam with said reference beam to form an electrical carrier, phase modulated as a result of said variation in the index of refracton,
      (e) a phase detector coupled to the output of said optical detector for detecting the acoustic wave induced phase variation of said sampling beam and thereby producing an electrical signal representative of the acoustic waves; and wherein
   B. each sensor is arranged so that the beam paths collectively form a closed polygon embracing said area.

* * * * *